United States Patent [19]

Levy

[11] Patent Number: 4,549,545

[45] Date of Patent: Oct. 29, 1985

[54] SEGMENTED POLYURETHANE SURGICAL BUTTRESSING PLEDGETS

[75] Inventor: Alan J. Levy, Bridgewater, N.J.

[73] Assignee: Ethicon Inc., Somerville, N.J.

[21] Appl. No.: 586,462

[22] Filed: Mar. 5, 1984

[51] Int. Cl.$^4$ .................. A61K 17/00; A61B 17/04
[52] U.S. Cl. ............................. 128/335; 128/335.5;
 604/372; 604/373
[58] Field of Search .............. 604/369, 370, 371, 372, 604/373, 374, 384; 128/335, 335.5

[56] References Cited

U.S. PATENT DOCUMENTS

| | | | |
|---|---|---|---|
| 4,043,331 | 8/1977 | Martin et al. | 128/156 |
| 4,044,404 | 8/1977 | Martin et al. | 120/156 |
| 4,127,124 | 11/1978 | Clagett et al. | 604/369 |

Primary Examiner—D. E. Gantz
Assistant Examiner—A. Pal
Attorney, Agent, or Firm—Charles J. Metz

[57] ABSTRACT

A surgical buttressing pledget for use with a suture wherein the pledget comprises a mat of continuous microfibers, wherein said microfibers consist essentially of a segmented urethane polymer.

11 Claims, 3 Drawing Figures

SEGMENTED POLYURETHANE SURGICAL BUTTRESSING PLEDGETS

The invention relates to surgical buttressing pledgets made from a mat of continuous spun microfibers of a segmented urethane polymer.

BACKGROUND OF THE INVENTION

There are a number of surgical procedures, particularly those involving the suturing of delicate bodily tissues, in which it is customary to employ a pledget or cushioning pad with the suture in order to prevent the suture strand from cutting into the tissue. For instance, see FIG. 6, part No. 40, of Cooley, U.S. Pat. No. 4,164,046, for a description of the use of pledgets in heart valve surgery. Such pads must combine the properties of softness, adequate tear strength, and tissue compatibility in order to be useable in this application. Typical materials that have been employed to produce such surgical buttressing pledgets in the past are pads of polytetrafluoroethylene or polyester felt, such as is described in Mandel et al., U.S. Pat. No. 4,034,850, and in Cooley, op. cit. supra.

While the polyester or the polytetrafluoroethylene felted materials that have been employed as pledgets in the past have served their purpose well, there is room for improvement. For instance, the felted materials can occasionally exfoliate (i.e., release particles), which is considered to be undesirable. Also, in many cases tissue will grow into, and in some cases all the way through, the felt, which is a disadvantage if the pledget must be removed. In a certain number of heart valve installations, the valve must be replaced. In such cases, tissue ingrowth is a definite disadvantage because it makes pledget removal difficult and annulus preparation for the new valve significantly more traumatic. One additional disadvantage of polytetrafluoroethylene pledgets is that they are degraded by gamma radiation to an extent that other means must be used to sterilize them.

The present invention is based upon the discovery that certain types of segmented urethane polymers can be converted to excellent surgical buttressing pledgets for use with sutures. Such pledgets are non-linting, are compatible with body tissues, are soft, have acceptable tear strength, and permit only limited tissue ingrowth so that if the pledget must later be removed, such removal is less traumatic than is the case with the present felted pledgets. They can also be sterilized by gamma radiation.

SUMMARY OF THE INVENTION

The invention provides a surgical buttressing pledget for use with sutures wherein tne pledget comprises a mat of continuous filament microfibers, wherein said microfibers consist essentially of a segmented urethane polymer.

THE PRIOR ART

U.S. Pat. Nos. 4,043,331 and 4,044,404, to Martin et al., disclose the preparation of continuous filament fibrous mats from electrostatically spun organic material, including urethane polymers (for instance, see Example 5 of each of the patents). Utilities mentioned for the mats include wound dressing, vascular prostheses, and filters.

U.S. patent application Ser. No. 291,649, filed in the name of Clarke and Gilding, for "Process For The Manufacture Of Polyurethane Resin For Electrostatic Spinning", filed on Aug. 10, 1981, discloses a process for the preparation of urethane resins that are particularly useful for electrostatic spinning. The assignee of this application is the joint assignee of the Clarke et al. application.

Clagett et al., in U.S. Pat. No. 4,127,124, disclose membranes of hydrophilic urethane polymers, which the patentees disclose can be used as bioimplant materials. In Example 1 of the Clagett et al. patent, the production of "pledgets" from this urethane membrane material is described. The patentees appear to be using the term "pledget" in its broader sense of being a compress or a tuft, rather than as the term is used herein to mean a buttress or cushion used with a suture. The urethane membranes described by Clagett et al. do not appear to be usable for the application contemplated herein.

DETAILED DESCRIPTION OF THE INVENTION

Figure 1:
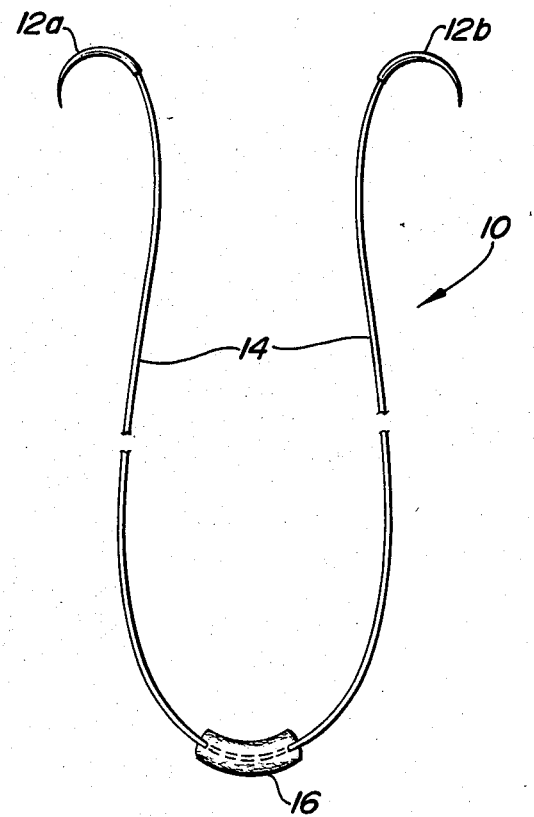
FIG. 1 is a perspective view of a needled suture with attached pledget.

The surgical buttressing pledgets employed in the invention are made from a continuous filament microfibrous mat. Such mats are preferably prepared by the electrostatic spinning of a segmented urethane polymer. Electrostatic spinning of properly constituted solutions of urethane polymers to form continuous filament mats of microfibers is a known technology. For instance, it is described in detail in the above-mentioned U.S. Pat. Nos. 4,043,331 and 4,044,404, the disclosures of which are incorporated herein by reference. Briefly, the process involves the introduction of a polymer solution in a suitable solvent into an electrostatic field where droplets of the solution are attenuated into fibers while being drawn to the surface of an electrode, which is usually in motion relative to the source of the solution droplets (e.g., a rotating mandrel), where the fibers are collected. The spinning conditions are controlled to evaporate the solvent while the fibers are being formed in the electrostatic field so that the fibers collected on the electrode retain their individual identity. Some fusing between fibers at points of intersection may occur, as a result of residual solvent content in the fibers. This is not necessarily disadvantageous. Residual solvent, if any, is removed from the mat of collected fibers as part of the total spinning process.

The fibers obtained by the electrostatic spinning process are very fine fibers, usually of the order of 0.1 to 25 microns in diameter, and more usually between 0.5 and 10 microns in diameter. For the purposes of this invention, the preferred size of the fibers is from about 1 to about 2 microns. For this application, the spinning process is controlled so as to provide a fibrous mat having a microporous structure or texture that resists tissue ingrowth (i.e., the individual pores have effective diameters of less than about 5 microns).

The urethane polymers employed in the invention are segmented urethane polymers having alternating soft segments and hard segments, that is, the urethane polymers are the well-known type that has been used for years in the production of the elastic fibers known as "Spandex". Suitable urethane polymers are described for instance, in U.S. Pat. Nos. 2,929,800, 3,428,711, 3,557,044, and 2,929,804. The polymerization reaction is essentially a two-step reaction, with the first step being the preparation of a prepolymer by reacting a polyester or polyether glycol having a molecular weight of at least about 200 with an excess of organic diisocyanate, to form an isocyanato-terminated prepolymer. The second step involves the reaction of the prepolymer with a difunctional extender, optionally with a very small proportion of a monofunctional material to act as a molecular weight regulator.

The diols that are employed in the invention are illustrated by poly(tetramethylene ether) glycols, usually having molecular weights above about 600, for instance, from about 800 to about 5,000. These materials are known articles of commerce; they are usually prepared by the condensation of tetrahydrofuran under appropriate conditions. This diol is then reacted with an organic diisocyanate, using a stoichiometric excess of the diisocyanate to form an isocyanto-terminated prepolymer. The isocyanates that are employed are usually aromatic isocyanates, such as 4,4'-diphenylmethane diisocyanate ("MDI"), or other materials such as tolylene diisocyanate. Diphenylmethane diisocyanate is the preferred diisocyanate.

The organic diisocyanate is employed in a stoichiometric excess over the diol. Typical proportions are from about 1.2 to about 1.9 moles of diisocyanate per mole of diol.

After the preparation of the prepolymer, the prepolymer is then reacted with a difunctional extender. Difunctional extenders are materials having, effectively, two groups which will react with isocyanate. Such extenders include dihydric alcohols, diamines wherein each amino group contains at least one amino hydrogen, and water. Normally, the difunctional extender is employed in the exact stoichiometric amount needed to react with all of the isocyanato groups in the prepolymer. Alternatively, the difunctional extender can be used in slightly less than stoichiometric proportions, and a monofunctional end-blocker such as methanol (or other lower alkanol) or an amine such as dibutylamine, diethylamine, or diisopropylamine, can be added along with the difunctional extender as a molecular weight regulator.

The difunctional extenders that can be employed in the invention include water, 1,4-butane diol, diethylene glycol, ethylene glycol, and other diols that are well known in the art, and diamines, preferably diamines having two primary amino groups, such as ethylene diamine, diphenylmethane diamine, and 1,3- or 1,4-cyclohexylene diamine.

In an alternative embodiment, additional diisocyanate can be added during the second reaction step in which the prepolymer is reacted with the difunctional extender. In such a case, an appropriate adjustment of the proportion of difunctional extender and, if present, monofunctional end-blocker, is made.

FIG. 1 shows a suture/pledget combination wherein the combination is identified by reference numeral 10, with the suture 14 being attached to needles 12a, 12b at each end, and being combined with the pledget 16. The pledget 16 is a mat of continuous filament microfibers consisting essentially of a segmented urethane polymer, as described herein. As shown in the drawing, the mat has two holes through which the suture 14 passes. The suture/pledget combination can be sterilized by conventional means such as by gamma radiation or ethylene oxide.

EXAMPLE

A segmented polyether-urethane is prepared by first reacting 4,4'-diphenylmethane diisocyanate with poly(tetramethylene ether) glycol in the molar ratio of about 1.7 moles of diisocyanate per mole of glycol to form an isocyanato-terminated prepolymer. The prepolymer is dissolved in a suitable solvent such as N,N-dimethylacetamide, and is then reacted with a stoichimetric amount of a mixture of 80 mole percent ethylenediamine and 20 mole percent 1,3-cyclohexylenediamine. If needed to regulate the molecular weight, a small (e.g., 5 to 10 mole percent, based on total diamines) of a mono-amine such as diethylamine may be added. The segmented polyetherurethane so prepared is used as an electrostatic spinning solution by preparing a 15 percent solids solution of the polymer in a mixture of N,N-dimethylacetamide and methyl ethyl ketone. In preparing the mat of continuous spun microfibers from which the pledgets of this invention are made, the poly(tetramethylene ether) glycol used to make the prepolymer has a molecular weight of about 1800. However, initiation of mat formation is facilitated if the polymer used in the beginning of the electrostatic spinning process is made from a higher molecular weight poly(tetramethylene ether) glycol, such as one having a molecular weight of about 3000.

Figure 3:
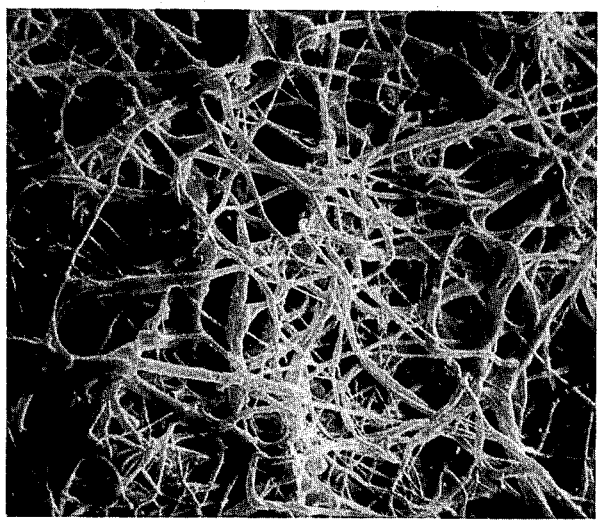

The above-described urethane polymer solution is used to electrostatically spin a mat of continuous spun microfibers. The collector is a rapidly rotating mandrel, such as is illustrated in FIG. 3 of Martin et al., U.S. Pat. Nos. 4,043,331 and 4,044,404. The dimensions of the mandrel are 5 centimeters in diameter by 20 inches long. The surface of the mandrel is smooth stainless steel. The polymer solution is fed through a manifold having several nozzles (e.g., seven nozzles). The nozzles are constructed similarly to hypodermic needles. The manifold oscillates in a direction parallel to the long axis of the mandrel. With an electrostatic potential of about 20 Kv., the distance between the tip of the nozzles and the surface of the rotating mandrel is between 5 and 35 centimeters. A warm air flow is maintained around the apparatus to facilitate evaporation of the solvents as the polymer solution is spun. Using this procedure, a mat of about one to one-and-one-half millimeters thick is produced. The density of the mat is about 0.55 grams per cubic centimeter, the porosity is about 43 percent, and the filament diameter is about one to two microns. Pledgets are cut from the mat. Typical dimensions of the pledgets are from one-quarter to three-eighths of an inch by one-eighth to three-sixteenths of an inch. They are essentially non-linting, have sufficient tear strength to prevent a suture from cutting through the pledget, and when implanted in a body, tissue ingrowth into the pledget is limited to a distance of about 40 microns or about 0.04 millimeter. This results in a flexible interface between the body tissue and the pledget, and makes later removal of the pledget (in those cases where indicated) much less traumatic than is the case when felted polyester or polytetrafluoroethylene pledgets are used.

Figure 2:
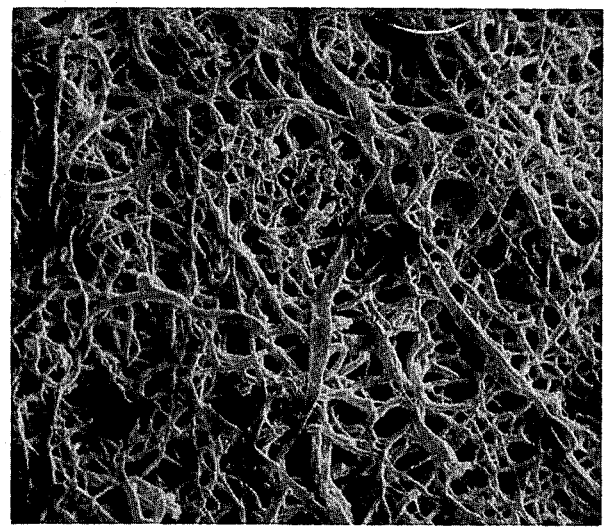
FIGS. 2 and 3 are photomacrographs, originally taken at 550×, of the two outside faces of a pledget made in accordance with the invention.

FIG. 2 is a photomacrograph of one face (the mandrel side) of a pledget of the invention, and FIG. 3 is a photomacrograph of the other face of the same pledget.

The microfiber orientation in the mats employed to produce the pledgets of the invention may be isotropic or it may be anisotropic. In the event that the microfiber orientation is anisotropic, the suture should be threaded through the pledget such that the suture is oriented in a direction about 90° from the predominant microfiber orientation. The direction of microfiber orientation of the mat can be determined by standard means, such as by determining the tensile strength in various directions in the plane of the mat. The direction that has the highest tensile strength is the direction of the predominant orientation of the microfibers.

What is claimed is:

1. A suture/pledget combination comprising a suture threaded through a perforated pledget, wherein the pledget comprises a mat of continuous filament microfibers, wherein said microfibers consist essentially of a segmented urethane polymer comprising the reaction product of a polyether or polyester glycol having a molecular weight of at least about 200, an organic diisocyanate, and a difunctional extender.

2. The suture/pledget combination of claim 1 wherein the glycol is a poly(tetramethylene ether) glycol having a molecular weight within the range of from about 800 to about 5,000.

3. The suture/pledget combination of claim 1 wherein the organic diisocyanate is an aromatic diisocyanate.

4. The suture/pledget combination of claim 3 wherein the aromatic diisocyanate is diphenylmethane diisocyanate.

5. The suture/pledget combination of claim 1 wherein the difunctional extender is a dihydric alcohol, a diamine containing two primary amino groups, or water.

6. The suture/pledget combination of claim 5 wherein the difunctional extender is 1,4-butane diol.

7. The suture/pledget combination of claim 1 wherein the reactants employed to produce the segmented urethane polymer includes a monofunctional end-blocker.

8. The suture/pledget combination of claim 1 wherein the orientation of the microfibers in said mat is anisotropic, and wherein said suture is threated through said pledget such that the suture is oriented in a direction substantially perpendicular to the direction of the predominant orientation of said microfibers.

9. The suture/pledget combination of any one of claims 1 through 8 in a sterile condition.

10. A surgical buttressing pledget adapted to be employed with a surgical suture, said pledget comprising a mat of continuous filament microfibers, wherein said microfibers consist essentially of a segmented urethane polymer comprising the reaction product of a polyether or polyester glycol having a molecular weight of at least about 200, an organic diisocyanate, and a difunctional extender.

11. The pledget of claim 10 in a sterile condition.

* * * * *